United States Patent [19]
Kristensen

[11] Patent Number: 5,843,379
[45] Date of Patent: Dec. 1, 1998

[54] SAMPLING DEVICE FOR A CHEMICAL ANALYSIS APPARATUS

[75] Inventor: Steen Gaardsted Kristensen, Nordborg, Denmark

[73] Assignee: Danfoss A/S, Nordborg, Denmark

[21] Appl. No.: 809,207

[22] PCT Filed: Sep. 4, 1995

[86] PCT No.: PCT/DK95/00354

§ 371 Date: Feb. 28, 1997

§ 102(e) Date: Feb. 28, 1997

[87] PCT Pub. No.: WO96/07885

PCT Pub. Date: Mar. 14, 1996

[30] Foreign Application Priority Data

Sep. 7, 1994 [SE] Sweden .................................. 9402980

[51] Int. Cl.$^6$ .............................. B01L 11/00; G01N 1/10
[52] U.S. Cl. .......................... 422/100; 422/61; 422/68.1; 422/69; 422/99; 422/112; 422/104; 210/90; 210/137; 436/179; 436/180
[58] Field of Search ............................... 422/58, 61, 68.1, 422/69, 99, 100, 102, 103, 104, 112; 210/90, 137, 416.1; 604/4, 6; 436/179, 180

[56] References Cited

U.S. PATENT DOCUMENTS

| | | | |
|---|---|---|---|
| 4,366,051 | 12/1982 | Fischel | ..................................... 210/96.2 |
| 4,432,806 | 2/1984 | Madsen et al. | ........................... 127/48 |
| 4,503,333 | 3/1985 | Kulin et al. | ........................... 250/455.1 |
| 4,552,552 | 11/1985 | Polaschegg et al. | ........................ 604/4 |
| 4,828,543 | 5/1989 | Weiss et al. | ................................ 604/4 |
| 5,372,709 | 12/1994 | Hood | ........................................ 210/90 |

FOREIGN PATENT DOCUMENTS

| | | |
|---|---|---|
| 0107631 | 5/1984 | European Pat. Off. . |
| 81/00911 | 4/1981 | WIPO . |
| 94/25875 | 11/1994 | WIPO . |

*Primary Examiner*—Harold Y. Pyon
*Attorney, Agent, or Firm*—Lee, Mann, Smith, McWilliams, Sweeney & Ohlson

[57] ABSTRACT

A sampling means of a chemical analysis apparatus includes a membrane, which is attached to a membrane carrier, which has an inlet passage to the side of the carrier facing the membrane and a discharge passage going therefrom. The passages conduct the medium to be measured and which medium absorbs ions, molecules or particles which pierce the membrane. In order to provide a sampling means, which has a short reaction time and makes use of small amounts of the medium to be measured and is easy to manufacture, the mouths of the inlet passage and of the discharge passage, which opens to the membrane, are interconnected by means of at least one groove, which is open towards the membrane. The groove is formed in a surface layer, which is attached between the membrane and the membrane carrier or is manufactured on the surface of the membrane carrier. The open side of the groove is closed by the membrane such that the membrane adheres to the surface layer or to the surface of the carrier facing the membrane.

8 Claims, 1 Drawing Sheet

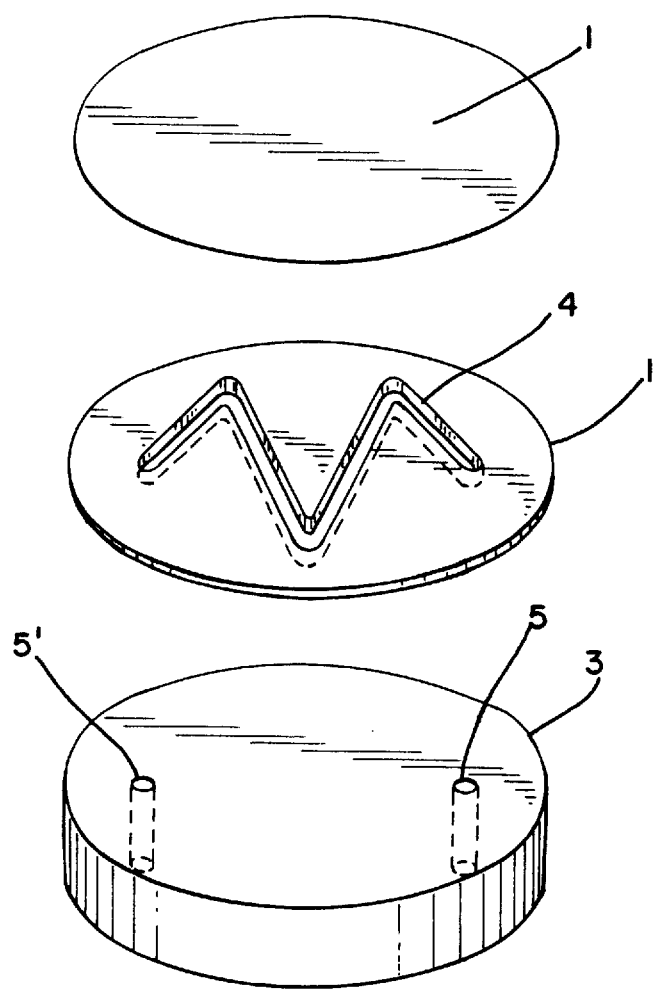

SAMPLING DEVICE FOR A CHEMICAL ANALYSIS APPARATUS

This application is a 371 of PCT/DK95/00354 filed on Sep. 4, 1995.

BACKGROUND OF THE INVENTION

This invention refers to a sampling device for a chemical analysis apparatus, which device comprises a diaphragm attached to a diaphragm carrier, which has an inlet channel to the side of the diaphragm facing the carrier and a discharge channel going therefrom, which channels conduct the medium to be measured. The medium absorbs ions, molecules or particles, which penetrate the diaphragm.

AT 355 546 discloses a known dialysis system of the kind mentioned in the introduction. For this purpose, the dialysis diaphragm is attached to the outside of a curved diaphragm carrier. A number of grooves forming channels are provided in the upper side of the diaphragm carrier. FR A 1 573 147 shows a similar device, however with a plane diaphragm carrier. A medium to be measured flows through the channels and ions from the surrounding medium penetrate the dialysis diaphragm into the medium to be measured, which is then sent to a chemical analysis apparatus. Through JP A 59 170 742 it is known to mount a plate in which the channels are arranged.

SUMMARY OF THE INVENTION

The object of the invention according to this application is to provide a sampling device, which has a short reaction time and makes use of small amounts of medium to be measured.

The sampling device according to the invention forms a small sample volume under the diaphragm where the sample volume has a large exposable upper surface facing the diaphragm. Thus, according to the invention, the depth of the groove or the channel is determined in a special way and this means that this parameter is easy to determine. Also the width of the groove can be determined exactly during the production.

The adhesive required to attach the diaphragm to the diaphragm carrier is at the same time used for forming the groove, which conducts the medium to be measured. The adhesive may be applied to the diaphragm carrier or to the diaphragm in such a way that areas are formed, which are kept free from adhesive and these areas are in connection with each other so that an open path is formed. The surface made as a layer of adhesive can alternatively be arranged between two layers of tape. This makes it possible to work the surface layer by water jet cutting or by punching in the same way as it is possible to form a groove in an adhesive double layer of tape.

In an embodiment the groove is formed in a surface layer e.g. a metal sheet and the groove is thus formed by punching, laser cutting, water jet cutting or etching of the metal layer.

The metal sheet or a sheet of a different material can be applied to the diaphragm carrier by means of an adhesive or the diaphragm can be clamped on the metal sheet and retained by the outside of the diaphragm carrier. This means that the sampling device can be made simply and cheaply. If the sheet is made of plastic the groove or grooves can be formed by punching or by water jet cutting. Laser cutting may also be possible. By using plastic for the sheet it is avoided that the metal emits ions to the medium to be measured, which a metal might do and if so the measurement would be deteriorated or destroyed in certain applications.

It is further suggested that the sheet is made from double-sided adhesive tape. A simple attachment to the diaphragm carrier and a correspondingly simple attachment of the diaphragm to the upper side of the sheet is hereby achieved. The double-sided adhesive tape may have a protecting tape over the layer of adhesive during production and a groove can then advantageously be formed by water jet cutting, which gives a high degree of freedom in forming the groove.

When the groove is formed in the sheet by etching there is also a large freedom concerning the shape of the groove.

Different types of diaphragms are used for different purposes. Thus, it is possible to use the diaphragm as a filter or different pressures can be used on the sides of the diaphragm for a reversed osmosis. The diaphragms may as well be used without a pressure difference for dialysis where ions penetrate the diaphragm and an equalization of the concentration of ions takes place on both sides of the diaphragm.

Advantageously, the sampling device according to the invention can be used in chemical analysis apparatuses, which are used for medical measurements. The sampling device is also applicable for measuring in the production in chemical industries. The invention can also be used when measuring the concentration of ions in waste water.

BRIEF DESCRIPTION OF THE DRAWING

A preferred embodiment of the invention among several ones will be described in the following with reference to enclosed drawing.

DESCRIPTION OF THE PREFERRED EMBODIMENTS

The drawing shows a diaphragm 1, and its characteristics determine the size or the chemical composition of particles, molecules or ions, which can penetrate the diaphragm. A sheet 2 a groove 4 is arranged under the diaphragm 1. In this case the sheet can be made from metal, plastic or adhesive and the groove can be produced by punching, etching, laser cutting or water jet cutting. The groove is shown in a certain zigzag pattern but the extension of the groove may be varied depending on the wanted length of the groove, the size of the areas etc. A diaphragm carrier 3 is shown under the sheet 2 in the FIGURE. The diaphragm carrier has an inlet channel 5 and a discharge channel 5'. The channels 5 and 5' are connected with each one end of the groove 4. This forms a flow path from the outside to the inlet channel 5, through the groove 4 and out through the discharge channel 5'.

Advantageously, the diaphragm 1, the sheet 2 and the diaphragm carrier 3 are glued together. The adhesive is applied on the sheet 2 before the groove 4 is formed, thus securing that the groove is free from adhesive. As mentioned, the sheet 2 may be a double-sided adhesive tape or adhesive, by which the adhesive surfaces are covered by a protecting tape during production.

As mentioned above the groove 4 may have different configurations depending on the application in question. There may also be several different grooves 4 under the same diaphragm and in connection with the inlet channel 5 and the discharge channel 5'.

I claim:

1. Sampling device for a chemical analysis apparatus for a medium, which device comprises a diaphragm attached to a diaphragm carrier, the device having an inlet channel on a side of a diaphragm facing the carrier and a discharge channel extending from the side of the diaphragm facing the carrier, which channels conduct the medium to be measured, and which medium absorbs ions, molecules or particles penetrating the diaphragm, by which openings of the inlet channel and of the discharge channel which open to the diaphragm are interconnected by means of at least one groove having an open side towards the diaphragm, the groove being formed in a surface layer which is located between the diaphragm and the diaphragm carrier, the open side of the groove being closed by the diaphragm and the diaphragm adhering to the surface layer.

2. Device according to claim 1, in which the diaphragm, the surface layer and the carrier have plane surfaces bearing against each other.

3. Device according to claim 2, in which the surface layer consists of an adhesive, in which at least one said groove is formed.

4. Device according to claim 1, in which the surface layer consists of a sheet.

5. Device according to claim 4, in which the sheet is made of metal.

6. Device according to claim 4, in which the sheet is made of plastic.

7. Device according to claim 4, in which the sheet is covered by an adhesive material on both sides.

8. Device according to claim 1, in which the surface layer consists of a fluid lining, which is applied on the carrier and which is hardened and adheres to the carrier.

* * * * *